United States Patent [19]

Oxford

[11] Patent Number: 6,083,995
[45] Date of Patent: Jul. 4, 2000

[54] 2,4-DICHLOROBENZYL ALCOHOL AND AMYLMETACRESOL AGAINST HIV INFECTION

[75] Inventor: John Sidney Oxford, London, United Kingdom

[73] Assignee: The Boots Company PLC, Nottingham, United Kingdom

[21] Appl. No.: 08/930,579

[22] PCT Filed: Apr. 18, 1996

[86] PCT No.: PCT/GB96/00928

§ 371 Date: Oct. 17, 1997

§ 102(e) Date: Oct. 17, 1997

[87] PCT Pub. No.: WO96/32934

PCT Pub. Date: Oct. 24, 1996

[30] Foreign Application Priority Data

Apr. 18, 1995 [GB] United Kingdom .................... 9507883

[51] Int. Cl.[7] .......................... A01N 31/00; A01N 31/08; A01N 25/34; A61F 6/06

[52] U.S. Cl. .......................... 514/730; 514/731; 424/430; 424/411

[58] Field of Search ...................... 514/730, 731; 424/411, 430

[56] References Cited

FOREIGN PATENT DOCUMENTS 0427997 5/1991 European Pat. Off. ....... A61K 31/00
2333849 1/1975 Germany .

OTHER PUBLICATIONS

Dr. W. Forth et al., Allg. und spezielle Pharmakologie und Toxikologie, 1983, Bibliographisches Institute Mannheim (translation).

Merck Index 10th Ed #8756+634, 1984.

Primary Examiner—Russell Travers
Attorney, Agent, or Firm—Arent Fox Kintner Plotkin & Kahn, PLLC

[57] ABSTRACT

The use of a composition comprising 2,4-dichlorobenzyl alcohol and amylmetacresol in the preparation of a medicament for the treatment or prevention of HIV viral infections.

16 Claims, No Drawings

2,4-DICHLOROBENZYL ALCOHOL AND AMYLMETACRESOL AGAINST HIV INFECTION

This Application is a 371 continuation of PCT/GB96/00928 filed Apr. 18, 1996 which claims priority from British Application 9507883.8 filed Apr. 18, 1995.

The present invention relates to the use of formulations of 2,4-dichlorobenzyl alcohol (or 2,4 DCBA) and amylmetacresol (or AMC) in the treatment or prevention of Human Immunodeficiency Virus (HIV) viral infections.

HIV infections are now found in every country in the world and the most important method of transmission is sexual. The virus is present as free virus particles or as intracellular virions in monocyte cells in semen. The virus is thereby transmitted relatively easily from male to female or male to male. Alternatively, in an infected female, virus either free or cell bound is found in fluid in the vagina.

Existing antivirals have been found which inhibit important enzymes of the virus such as reverse transcriptase (RT), protease or integrase. The first clinically used drug namely AZT (or zidovudine, Retrovir™), inhibits the virus RT enzyme. However, AZT does not represent a cure of infection and has not been demonstrated to prevent person to person spread. Indeed one of the clinical problems with the drug, apart from toxicity, is the emergence of drug resistant virus and the actual spread of the drug resistant virus in the community. A new approach against HIV is therefore to search for novel compounds which may destroy or inactivate free virus and/or cell associated virus directly on contact. These are so-called virucidal compounds. Such molecules have been described in the past (Oxford et al in App. Microbiology 21 606–610 (1971)), but have been little investigated recently.

Since the HIV virion is surrounded by a lipid bilayer it would be logical to test detergent like molecules for their ability to disrupt and dissolve the lipid membrane of the virus. For example the non-ionic surfactant nonoxynol-9 has been used in clinical practice as a spermicide and has direct anti-HIV activity (Malkovsky et al in *The Lancet* 645 (1988)). However, it has little selective anti-HIV effect and because it causes toxicity and cell destruction following application to the vagina its use may actually enhance infection with HIV (Kreiss et al in *J.A.M.A.* 268 477–482 (1992)).

The compound 2,4-dichlorobenzyl alcohol is known as an antiseptic agent i.e. as an antibacterial and antifungal agent, see for example Martindale "The Extra Pharmacopoeia" 28th edition, page 561, The Pharmaceutical Press (1982). Amylmetacresol or 6-pentyl-m-cresol is also known as a disinfectant used in mouth-washes or lozenges in combination with 2,4-dichlorobenzyl alcohol to treat mouth infections, see for example Martindale "The Extra Pharmacopoeia" 28th edition, page 549, The Pharmaceutical Press (1982). An antiseptic is defined in The Concise Oxford Dictionary (Oxford University Press, Oxford (1982)) as an agent which counters the development of sepsis, especially by preventing the growth of bacteria. Sepsis is defined in Black's Medical Dictionary (A & C Black, London (1990)) as poisoning by the products of the growth of microorganisms in the body, and the general symptoms which accompany it are those of inflammation. Neither 2,4-dichlorobenzyl alcohol or amylmetacresol has previously been shown to demonstrate anti-viral or anti-retroviral activity and, in particular, anti-HIV activity.

Unexpectedly it has now been discovered that a formulation of 2,4-dichloroberzyl alcohol and amylmetacresol has anti-retroviral activity and causes inactivation of HIV infectivity.

According to the present invention there is provided the use of a composition comprising 2,4-dichlorobenzyl alcohol and amylmetacresol in the preparation of a medicament for the treatment or prevention of HIV viral infections.

In a particularly preferred embodiment of the present invention there is provided the use of a Strepsil™-like formulation of 2,4-dichlorobenzyl alcohol and amylmetacresol in the preparation of a medicament for the treatment or prevention of HIV viral infections.

The pharmaceutical composition may be adapted for administration by any appropriate route, for example by the vaginal, rectal or oral routes. Such compositions may be prepared by any method known in the art of pharmacy, for example by admixing the active ingredient with the carrier(s) or excipient(s) under sterile conditions.

For the preparation of solutions and syrups used in formulating the composition, excipients which may be used include for example water, polyols and sugars. For the preparation of suspensions oils (e.g. vegetable oils) may be used to provide oil-in-water or water in oil suspensions. Other suitable excipients include for example vegetable oils, waxes, fats, semi-solid, or liquid polyols etc.

Alternatively the composition may be formulated as an ointment, cream, suspension, lotion, powder, solution, paste, gel, spray, aerosol or oil. When formulated in an ointment, the active ingredient may be employed with either a paraffinic or a water-miscible ointment base. The active ingredient may also be formulated in a cream with an oil-in-water cream base or a water-in-oil base. Compositions may be further prepared in which the active ingredients are dissolved or suspended in a suitable carrier, especially an aqueous solvent.

Pharmaceutical compositions adapted for vaginal administration may be presented as pessaries, tampons, creams, gels, pastes, foams or spray formulations. Pharmaceutical compositions adapted for rectal administration may be presented as suppositories or enemas.

It also contemplated that the compositions may include anti-oxidants, buffers, bacteriostats, solutes, suspending agents and thickening agents. Excipients which may be used include water, alcohols, polyols, glycerine and vegetable oils, for example.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the age and condition of the individual to be treated, etc. and a physician will ultimately determine appropriate dosages to be used. However, without being bound by any particular dosages, it is believed that, for vaginal, rectal or oral administration, an effective composition in accordance with the present invention (usually present as part of a pharmaceutical composition as discussed above) may be suitable in treatments of the present invention as follows:

Suitable concentration ranges for the compounds present in the composition may be as follows. 2,4-dichlorobenzyl alcohol may be present in the composition in a concentration of from 10 µg/ml to 10 mg/ml, preferably of from 0.1 mg/ml to 5 mg/ml and particularly of from 1.0 mg/ml to 5 mg/ml. The concentration of amylmetacresol in the composition may be of from 10 µg/ml to 5.0 mg/ml, preferably from 50 µg/ml to 2.0 mg/ml and particularly from 0.05 mg/ml to 1.0 mg/ml. If side effects develop, the amount and/or frequency of application of the composition can be reduced, in accordance with normal clinical practice.

In the context of the present invention the term "HIV" extends to HIV-1, HIV-2 and other related viruses responsible for the medical condition described as Acquired Immunodeficiency Syndrome (AIDS) or the condition described as AIDS-Related Complex (ARC). The term HIV is the internationally accepted definition of the viruses previously known by the names HTLV-III, LAV and ARV.

Alternatively, the invention provides the use of 2,4-dichlorobenzyl alcohol and/or amylmetacresol in the preparation of a medicament for the treatment or prevention of viral infections caused by HIV.

The use of a formulation of 2,4-dichlorobenzyl alcohol and amylmetacresol in an acidic sucrose base in the preparation of a medicament for the treatment or prevention of viral infections caused by HIV is also in accordance with the present invention.

It is also part of the present invention to provide the use of a composition comprising 2,4-dichlorobenzyl alcohol and/or amylmetacresol in the preparation of an agent for the treatment or prevention of HIV viral infections. The agent may a barrier contraceptive device, or it may adapted for vaginal or rectal administration.

The present invention, therefore, also extends to a method of treatment or prevention of HIV viral infections, the method comprising administration of an effective amount of 2,4-dichlorobenzyl alcohol and/or amylmetacresol.

Compositions of the present invention may be suitably used for vaginal, rectal or oral administration. Where the route of administration is vaginal, the composition may be provided in the form of a pessary, cream, gel, lotion or spray. Where the route of administration is rectal, the composition may be provided in the form of an enema.

Since an identical formulation has been used for two decades or more as Strepsil™ mouth lozenges to combat bacterial infections it is speculated that the mixture has little deleterious effect on mucosal cells in this region. It is proposed that should such an absence of cellular toxicity in a human mucosal surface be accompanied by the virucidal effects now discovered against HIV-1, that the formulation or a similar formulation could be used as vaginal or rectal application, or as a constituent in a barrier contraceptive device to inactivate HIV on contact, or used orally to destroy extra-cellular virus and hence reduce or prevent spread of the virus. Such a composition or a barrier contraceptive device containing such a composition may also contain other active agents, for example a spermicide. The barrier contraceptive device may also be provided with a lubricant, such as for example Vaseline™ or KY Jelly™.

Barrier contraceptive devices include the male sheath or condom, the cap and the female condom or Femidom™. As described above it is also contemplated that compositions according to the present invention could be applied to or contained in such devices.

Thus, in other aspects the invention provides (a) a composition of the invention for use in vaginal, rectal or oral application or to be applied to a barrier contraceptive device, such as a condom or cap; and (b) a barrier contraceptive device, such as a condom or cap, incorporating a composition of the invention.

The present invention also includes a product comprising 2,4-dichlorobenzyl alcohol and amylmetacresol as a combined preparation for simultaneous, separate or sequential use in the treatment or prevention of HIV viral infections.

Compositions according to the present invention may also be used as part of a kit comprising a barrier contraceptive device, such as a condom or cap, and optionally a spermicide and/or a lubricant, for example Vaseline™ or KY Jelly™. The spermicide may also be formulated in any convenient form such as a gel, cream or spray for subsequent application as part of the kit.

Preferred features of the invention for the second and subsequent features of the invention are as for the first aspect *mutatis mutandis*.

The invention will now be described by way of example with reference to the accompanying Examples which are provided for the purposes of illustration and are not to be construed as being limiting on the present invention.

EXAMPLE 1

Preparation of Virucidal Mixture

A virucidal mixture for use in the in vitro activity assays was prepared as follows. A commercial preparation of a tablet containing 1.6 mg 2,4-dichlorobenzyl alcohol (2,4-DCB alcohol) and 0.6 mg amylmetacresol (AMC) B.P. was mixed into 5 ml of buffered saliva. This preparation containing the active factors is known as the virucidal mixture).

EXAMPLE 1

In Vitro Activity

Virus: Laboratory Isolate of HIV-1, MN Cells: C8166-cells

A sample of HIV-1 was added to a preparation of 2,4-dichlorobenzyl alcohol (2,4-DCB alcohol) and amylmetacresol (AMC) in 5 ml of buffered saliva (the virucidal mixture). A corresponding sample of HIV-1 was separately added to 5 ml of untreated buffered saliva (the control mixture) -The two mixtures containing virus were incubated for periods of 2, 4, 20 and 60 minutes at 37° C. At these particular time periods a sample of virus was removed from each of the two mixtures and titrated in susceptible C8166-cells for residual virus infectivity. The compound was not toxic to C8166-cells. The experiment was repeated four times using different quantities of HIV-1 in the mixture.

Results

The results for the experiments are shown below in Table 1 and Table 2. The quantity of infective virus remaining in the mixture is expressed as syncytium inducing units of virus per ml.

TABLE 1

Initial virus concentration = $10^6$ $ID_{50}$/ml

| Incubation time (mins) | Quantity of infective virus remaining/2,4-DCB alcohol and AMC mixture | Quantity of infective virus remaining/ Control mixture |
|---|---|---|
| 2 | ≦100 | 1,000,000 |
| 4 | ≦100 | 1,000,000 |
| 20 | ≦100 | 1,000,000 |
| 60 | ≦100 | 1,000,000 |

TABLE 2

Initial virus concentration = $10^5$ $ID_{50}$/ml

| Incubation time (mins) | Quantity of infective virus remaining/2,4-DCB alcohol and AMC mixture | Quantity of infective virus remaining/ Control mixture |
|---|---|---|
| 2 | ≦100 | 100,000 |
| 4 | ≦100 | 100,000 |
| 20 | ≦100 | 100,000 |
| 60 | ≦100 | 100,000 |

The experiments, whose results are shown in Table 1 and is Table 2, commenced by incubation of either $10^6$ or $10^5$ infective syncytium inducing units of HIV-1 with the two mixtures. The solution containing the 2,4-DCB and AMC preparation caused a $10^3$–$10^4$ fold reduction of infectivity (syncytium inducing activity) of the virus in both experiments. Note that HIV induces cell fusion (or syncytia) in susceptible cells and that this is used as a useful and accurate estimate of the infectious ability of the virus.

EXAMPLE 2
Effect of PH on in Vitro Activity

In further experiments we investigated the effect of pH on the virucidal effect of the mixture. A low pH was necessary for the anti-HIV activity of the preparation but low pH by itself did not abolish virus infectivity. Incubation of virus with 30% sucrose had no virucidal effect.

The in vitro data describes the surprising ability of a mixture of two organic molecules in an acid solution containing sucrose and additional ion constituents to very significantly reduce the infectivity of live infectious HIV-1. The compounds contained in the preparation may act to together with possible synergistic results or they may have separate activities. It may be that they exert their activity by binding to the outside protein spikes of the virus to thereby abolish absorption of the virus to an indicator cell, by clumping virus, by partial denaturation of the spike protein, by an action on the lipid bilayer or by stabilising virus structure (OxFord and Thomas in *Principles of Bacteriology Virology and Immunology* 4 (1990) Published by Edward Arnold).

The anti-HIV efficacy of the mixture may be improved by reformulation or addition of similar molecules, but the current formulation has the advantage of extensive clinical database following the application of the 2,4-dichlorobenzyl alcohol and anylmetacresol mixture on mucosal surfaces of man to prevent or treat sore throats caused by bacterial infection.

EXAMPLES 3

Virucidal Activity of 2.4 DCBA and AMC Formulations

The anti-HIV effects of varying concentration of AMC and DCBA were also separately studied. The results of these experiments are show-n in Tables 3 to 5.

Materials and Methods

Test Reagent

AMC was purchased as a dark-yellow solution and was dissolved first in DMSO and then further dilutions were made in artificial saliva (2.4 mg/ml, 1.2 mg/ml, 0.12 mg/ml, 0.06 mg/ml, 0.03 mg/ml, 0.015 mg/ml and 0.0075 mg/ml). DCBA was Purchased as white powder and dissolved in DMSO (100 mg/ml stock) and further dilutions were made in artificial saliva (4.8 mg/ml, 2.4 mg/ml, 0.24 mg/ml, 0.12 mg/ml, 0.06 mg/ml, 0.03 mg/ml and 0.015 mg/ml).

Cell Cultures

Human T-cell line C8166 was used for virucidal tests and cells were cultivated in RPMI 1640 medium (from Sigma Chemical Company, UK) supplemented with 10% heat-inactivated (56° C., 30 mins) foetal calf serum (FCS), 2 mM L-glutamine, 100 U/ml penicillin, 100 μg/ml streptomycin and $5\times10^{-5}$ m 2-Mercaptoethanol (Sigma Chemical Company, UK).

Virus Stock

A stock of laboratory strain HIV-$1_{IIIB}$ containing cell free tissue culture supernatant, stored in liquid nitrogen, was used in the assays. Before and after freezing the virus stock was titrated to ensure the correct $TCID_{50}$ required for the particular assay.

EXAMPLE 3

Virucidal Assay

Lymphoblastoid C8166 cells were plated out into 96 well plates (180 μl/well) at a concentration of $5\times10^5$ per ml in six-replicate in growth medium. Different concentrations of the compounds were mixed with a high titre of HIV-$1_{IIIB}$ ($10^6$ $TCID_{50}$) at a ratio of 1:10 (1 ml total) and were incubated at 37° C. for one or fifteen minutes. After incubation, the mixture of virus/compound (20 μl) was added to the fop row of C8166 cells. After mixing, then 20 μl was transferred into the next series of wells etc., to give a ten-fold dilution series from $10^{-1}$ to 10 and the plates were incubated at 37° C. for 10 days.

TABLE 3

Initial virus concentration $10^5$ $ID_{50}$/ml MN

| Quantity of infective virus remaining after 1 minute at 37° C. | Quantity of infective virus remaining after 1 minute at 37° C. | | | Quantity of infective virus remaining in control mixture |
|---|---|---|---|---|
| 0.24 mg/ml 2,4 DCBA and 0.12 mg/ml AMC mixture | 0.24 mg/ml 2,4 DCBA | 0.12 mg/ml AMC | low pH alone | |
| <10 | <10 | <10 | <10 | 100,000 |

TABLE 4

Initial virus concentration $10^5$ $TCID_{50}$/ml MN

| Quantity of infective virus remaining after 1 min at 37° C. with AMC at varying concentrations (mg/ml) | | | | Quantity of infective virus remaining in control mixture |
|---|---|---|---|---|
| 0.06 | 0.03 | 0.015 | 0.0075 | |
| <10 | 10 | 1000 | 100,000 | 100,000 |

TABLE 5

Initial virus concentration $10^5$ $TCID_{50}$/ml MN

| Quantity of infective virus remaining after 1 min at 37° C. with AMC at varying concentrations (mg/ml) | | | | Quantity of infective virus remaining in control mixture |
|---|---|---|---|---|
| 0.24 | 0.12 | 0.06 | 0.03 | |
| <10 | <10 | 10 | 1000 | 100,000 |

What is claimed is:

1. A method of preventing an HIV viral infection, the method comprising administering effective amounts of 2,4-diclorobenzyl alcohol and amylmetacresol to a host in need of such prevention.

2. The method of claim 1 wherein 2,4-diclorobenzyl alcohol and amymetacresol are administered vaginally, rectally or orally.

3. The method of claim 1 wherein 2,4-diclorobenzyl alcohol and amymetacresol are administered in the form of pessary, enema, cream, gel, spray or lotion.

4. The method of claim 1 wherein 2,4-diclorobenzyl alcohol and amymetacresol are applied to a barrier contraceptive device.

5. The method of claim 4 in which the barrier contraceptive device is a condom or cap.

6. The method of claim 1 wherein 2,4-diclorobenzyl alcohol and amymetacresol are administered in an acidic sucrose base.

7. The method of claim 1, wherein 2,4-diclorobenzyl alcohol and amymetacresol are administered orally.

8. A barrier contraceptive device incorporating a composition comprising 2,4-dichlorobenzyl alcohol and amylmetacresol.

9. The barrier contraceptive device of claim 8 which is a condom or a cap.

10. A kit comprising a barrier contraceptive device, 2,4-dichlorobenzyl alcohol and amylmetacresol.

11. The kit of claim 10, in which the barrier contraceptive device is a condom.

12. The kit of claim 10, further comprising a spermicide and/or a lubricant.

13. A method of treating an HIV viral infection, the method comprising administering effective amounts of 2,4-diclorobenzyl alcohol and amylmetacresol to need of such treatment.

14. The method of claim 13, wherein 2,4-diclorobenzyl alcohol and amymetacresol are administered vaginally, rectally or orally.

15. The method of claim 13, wherein 2,4-diclorobenzyl alcohol and amymetacresol are administered in the form of pessary, enema, cream, gel, spray or lotion.

16. The method of claim 13, wherein 2,4-diclorobenzyl alcohol and amymetacresol are administered in an acidic sucrose base.

* * * * *